United States Patent [19]
McKnight

[11] Patent Number: 5,633,152
[45] Date of Patent: May 27, 1997

[54] METHOD OF CONTROLLING VIRAL GROWTH

[75] Inventor: Steven L. McKnight, Baltimore, Md.

[73] Assignee: Carnegie Institution of Washington, Washington, D.C.

[21] Appl. No.: 280,247

[22] Filed: Jul. 25, 1994

Related U.S. Application Data

[63] Continuation of Ser. No. 210,904, Jun. 24, 1988, abandoned, which is a continuation of Ser. No. 963,015, Oct. 19, 1992, abandoned.

[51] Int. Cl.$^6$ ............................ C12N 7/01; C12N 15/38
[52] U.S. Cl. .................................. 435/172.3; 435/235.1
[58] Field of Search ........................... 435/172.3, 235.1, 435/236, 238; 935/1, 9, 10, 34

[56] References Cited

U.S. PATENT DOCUMENTS

| | | | |
|---|---|---|---|
| 4,774,182 | 9/1988 | Szybalski | 435/69.1 |
| 4,859,587 | 8/1989 | Roilzman | 424/199.1 |
| 5,245,010 | 9/1993 | Greaves | 530/327 |

OTHER PUBLICATIONS

Preston et al, 1988 Cell 52 425–435.
McKnight et al 1980 Nucleic Acids Research.
Preston et al, Cell 52: 425–434, 1988 (Jan. 12, 1988).
McKnight et al NAR 24:5931. 1980.
Preston et al Cell 52: 425–434, 1988 (Feb. 12, 1988).
McKnight et al NAR 24:5931. 1980.

*Primary Examiner*—Robert A. Wax
*Assistant Examiner*—Gabriele E. Bucaisky
*Attorney, Agent, or Firm*—Cushman Darby & Cushman, L.L.P.

[57] ABSTRACT

The present invention relates to a method of specifically inhibiting the growth of a virus, particularly an animal virus, in a permissive host cell comprising introducing into the host cell a virus-related gene encoding a product capable of interacting with the genome of the infecting virus (or a product encoded therein) in a manner such that the life cycle of the infecting virus is disrupted. The invention also relates to a method of rendering a cell, particularly an animal cell, resistant to viral infection, and to a viral resistant cell.

3 Claims, 1 Drawing Sheet

```
              ┌AN'C→
H₂N- M D L L V D E L F A   D M D A D G A S P P   P P R P A G G P K N   T P A A P P L Y A T    40
      G R L S Q A O L M P   S P P M P V P P A A   L F N R L L D D L G   F S A G P A L C T M    80
       └─┬─┘               └─┬─┘                     └┬┘
         41                   56                      74
      L D T W N E D L F S   A L P T N A D L Y R   E C K F L S T L P S   D V V E W G D A Y V   120
      P E R A Q I D I R A   H G D V A F P T L P   A T R D G L G L Y Y   E A L S R F F H A E   160
      L R A R E E S Y R T   V L A N F C S A L Y   R Y L R A S V R Q L   H R Q A H M R G R D   200
      R D L G E M L R A T   I A D R Y Y R E T A   R L A R V L F L H L   Y L F L T R E I L W   240
      A A Y A E Q M M R P   D L F D C L C C D L   R S W R Q L A G L F   Q P F M F V N G A L   280
      T V R G V P I E A R   R L R E L N H I R E   H L N L P L V R S A   A T E E P G A P L T   320
                                                        380
      T P P P T L H G N Q A   R A S G Y F M V L I   R A K L D S Y S S F   T T S P S E A V M R   360
                                                         └┬┘
                                              393
      E H A Y S R A R T K   N N Y G S T I E G L   L D L P D D D A P E   E A G L A A P R L S   400
       └┬┘                                                               └┬┘
        363                                                                439
                           ┌ANC→                              429            ┌─┴─┐
      F L P A G H T R R L   S T A P P T D V S L   G D E L H L D G E D   V A M A H A D A L D   440
                             └──┬──┘                          469
                              ←ΔC┘                           456
      D F D L D M L G D G   D S P G P G F T P H   D S A P Y G A L D M   A D F E F K Q H F T   480
       └┬┘
        443
                488 490
      D A L G I D E Y G G - COOH
                   └─┬─┘
                    ←ΔC┘
```

METHOD OF CONTROLLING VIRAL GROWTH

This application is a continuation of U.S. Ser. No. 07/963,015 filed on Oct. 19, 1992 now abandoned which is a continuation of application Ser. No. 07/210,904 filed Jun. 24, 1988, now abandoned.

BACKGROUND OF THE INVENTION

1. Technical Field

The present invention relates, in general, to a method of controlling the growth of a virus and, in particular, to a method of controlling viral growth by causing a viral gene product, or derivative thereof, to be produced in a permissive host in a manner that results in disruption of the vital life cycle.

2. Background Information

Viral infection of a host cell commences with attachment of the virus to the cell surface and subsequent penetration of the genetic material of the virus (DNA or RNA) into the cytoplasm of the host cell. The viral genetic material crosses the plasma membrane of the cell either alone or in association with inner viral proteins. The DNA of most animal viruses is eventually found in the cell nucleus where it can interact with the host cell's nucleic acid synthesizing machinery to produce viral mRNA. This mRNA is then transported to the cytoplasm where viral proteins are synthesized. The vital protein products are used in the construction of new virus particles. Completed viral particles are released either upon rupture of the infected host cell or by gradual exocytosis via intracellular transport systems. Release of the viral particles completes one cycle of the lytic stage of vital growth.

A second stage of vital growth, displayed by certain viruses, is the latent phase. During this stage, viral DNA is stably maintained in the nucleus and is replicated as the host cell grows and divides. While many DNA viruses become integrated into the host chromosome, others are maintained extrachromosomally. In the case of retroviruses, a cDNA is transcribed from the retroviral RNA template and subsequently integrated into the host genome. In response to ill-defined "inducing events", viral DNA can emerge from its latent state and again enter the lytic cycle.

Central to viral infection and growth are:

1) the temporal expression of viral genes in response to specific viral regulators, and 2) the specific and ordered interaction of the products of that gene expression. Recent developments in molecular genetics and gene transfer techniques have made it possible to study the mechanisms underlying both of these aspects of virus production. The use of these same techniques to impart viral resistance has proven successful in plants. Specifically, insertion of a cDNA of Tobacco Mozaic Virus (TMV) coat protein gene results both in the expression of that protein at a level of approximately 0.1% of the total leaf protein of the transgenic tobacco and in the acquisition of resistance to infection by TMV (Able et al *Science* 232:738 (1986)). The ability to confer viral resistance on animals, either by direct gene transfer or germ line transformation, would provide a new and powerful tool for use in the prevention and treatment of specific types of viral infections.

OBJECTS OF THE INVENTION

It is an object of the invention to provide a method of rendering cells, preferably animal cells, resistant to viral infection.

It is also an object of the invention to provide a method of specifically inhibiting viral growth in a manner which does not exert a deleterious effect on the host cell.

It is another object of the invention to provide a trans-dominant form of a virus-specific activator protein which, when expressed in a permissive cell, is capable of conferring viral resistance.

It is a further object of the invention to provide a genetically transformed viral resistant animal cell.

Further objects and advantages of the invention will be apparent to one of ordinary skill in the art from the following detailed description thereof.

SUMMARY OF THE INVENTION

In one embodiment, the present invention relates to a method of specifically inhibiting growth of a virus in a permissive host cell comprising:

i) introducing into the host cell a virus-related gene encoding a product capable of specifically interacting, directly or indirectly, with the genome of the infecting virus (or a product encoded therein) so that the life cycle of the infecting virus is disrupted; and ii) causing expression of the virus-related gene and interaction of the product of that expression with the genome of the infecting virus (or product encoded therein).

In another embodiment, the invention relates to a method of rendering a cell resistant to infection by a virus comprising:

i) introducing into the cell a virus-related gene encoding a product capable of specifically interacting with the genome of the infecting virus (or product encoded therein) so that the life cycle of the infecting virus is disrupted; and ii) causing expression of the virus-related gene and interaction of the product of that expression with the genome of the infecting virus (or product encoded therein).

In yet another embodiment, the present invention relates to a cell resistant to a virus, which cell comprises a virus-related gene product capable of interacting with the genome of the infecting virus (or product encoded therein) so that the life cycle of the infecting virus is disrupted.

BRIEF DESCRIPTION OF THE DRAWING

The FIGURE shows the amino acid sequence of VP16 deduced from the nucleotide sequence of the VP16 gene.

DETAILED DESCRIPTION OF THE INVENTION

The invention relates to a method of specifically inhibiting viral growth. The method comprises introducing into a cell harboring a virus, or a cell subject to viral infection, a virus-related gene encoding a product capable of specifically interacting, directly or indirectly, with the viral genome itself, or with a product encoded therein, in a manner such that disruption of the viral life cycle results. Such disruption can be effected: 1) by causing a normal viral gene product to be produced at an inappropriate time or in an inappropriate quantity, or 2) by causing an aberant form of a viral gene product to be produced.

The viruses to which the invention relates are, preferably, those which infect animals, most preferably, mammals, including humans. Examples include herpes simplex viruses (HSV) and human immunodeficiency virus (HIV).

As indicated above, the product encoded in the sequence introduced into the permissive cell is either: 1) one which specifically interacts, directly or indirectly, with the viral genome and thereby affects viral gene expression, or 2) one which specifically interacts with a viral gene product normally produced during infection; the interaction can, for example, be one which inhibits the formation of mature viral particles. Advantageously, the above-described product specifically (that is, without harm to the host) "poisons" molecules that potentiate: 1) transcription of viral genes, 2) translation of viral mRNA into protein, 3) replication of viral DNA, 4) assembly of viral particles, 5) exocytosis of viral particles, or 6) subsequent viral infection.

In one embodiment, the encoded product is a protein that controls (that is, activates or represses) viral gene expression. Advantageously, the protein is a trans-dominant form of a viral activator, for example, a form of the HSV-specific activator VP16 lacking the activating domain (see the following Examples), or a form of the HIV-specific activator TAT capable of dimerizing with native TAT and thereby preventing formation of the activating complex (see Frankel et al. *Science* 240:70 (1988)).

The sequence encoding the product (i.e., protein) of the invention can be introduced into the host, or potential host, cell using techniques well known in the art. For example, it is contemplated that HIV resistance can be conferred by introducing a trans-dominant form of TAT into isolated human T cell and/or macrophage precursors using, for example, retrovirus transfection vectors. The transformed T cells can then be transplanted into an HIV-infected patient using standard bone marrow transplant protocols. As a further example, it is anticipated that herpes virus resistant animals (for example, cows, horses and pigs) can be produced by introducing a gene encoding a trans-dominant form of a vital regulatory protein into the germ line of an animal in a manner such that it will be incorporated into the chromosome in an active state. Methods of germ line transformation are the subject of a recent review article by R. Jaenisch (*Science* 240:1468 (1988); the entire contents of which document (and articles cited therein) are hereby incorporated by reference and relied upon).

The following non-limiting Examples illustrate the invention in more detail.

EXAMPLE 1

Identification of and Production of a Trans-Dominant Form of a Viral Regulatory Gene DNA sequences closely associated with intermediate early (IE) genes of HSV-1 are required for response to trans-activation by VP16, a virus-encoded activating protein. For example, a 220 base pair region upstream of the IE gene that encodes ICP4 (infected cell protein 4) acts as a transcriptional enhancer (Langet al. *EMBO* 3:389 (1984); Preston and Tannahill *Virology* 137:439 (1984); Puga et al. *J. Virol.* 54:879 (1985)). This 200 bp region contains two distinct cis-regulatory motifs that mediate trans-activation by VP16. One such motif, identified in several different studies (Mackem and Roizman *J. Virol.* 44:939 (1982); Cordingley et al. *Nucleic Acids Res.* 11:2347 (1983); Kristie and Roizman *Proc. Natl. Acad. Sci. U.S.A.* 81:4065 (1984)), has easily-recognized counterparts upstream of each of the viral IE genes, and is characterized by the nonanucleotide sequence 5'-TAATGARAT-3' (R=purine). A second cis regulatory motif within the ICP4 enhancer that specifies response to VP16 has been recently identified by Applicants (Triezenberg et al., *Genes and Devel.* (1988)). The sequence of this second element is purine rich and typified by direct repeats of the hexanucleotide sequence 5'-GCGGAA-3'. Either of these two cis motifs can act independently to mediate trans-activation by VP16, but maximal induction depends on the presence of both.

Purified VP16 displays no substantial affinity for double stranded DNA (Marsden et al. *J. Virol.* 61:2428 (1987)). Instead, host-cell proteins bind in a sequence specific manner to the IE cis response elements (Kristie and Roizman *Proc. Natl. Acad. Sci. USA* 84:71 (1987); Preston et al. *Cell* 52:425 (1988); Triezenberg et al. *Genes and Devel.* (1988)). Applicants have shown that two distinct host factors exist which bind specifically to the two cis motifs that mediate VP16-dependent induction of IE gene transcription (TAATGARAT and GCGGAA).

To determine the molecular basis of VP16 action, in vitro mutagenesis was used to delete terminal or internal portions of the VP16 open reading frame (ORF). Mutated VP16 genes were tested in a transient co-transfection assay that measured trans-induction of IE gene expression. As a result of these studies it was established that loss of one domain located within the carboxy terminal 78 amino acids of VP16 resulted in a loss of the ability to trans-activate IE gene expression.

To test whether non-activating deletions such as ΔC439-490 (see FIG. 1) might act in a dominant manner, cultured mouse L cells were transfected with the indicator plasmid (pICP4tk), the internal control plasmid (pMSVtk), and varying amounts of ΔC439-490. This derivative of the parental VP16 template encodes a truncated polypeptide that is incapable of trans-activating pICP4tk. Two days later, the transfected cells were super-infected with HSV-1 as a means of introducing native, virus-encoded VP16. RNA was then purified from each culture plate and assayed by primer extension for expression from pICP4tk and pMSVtk. As the amount of ΔC439-490 was increased, expression from pICP4tk decreased. Indeed, VP16-mediated trans-induction was eliminated when as little as one microgram of ΔC439-490 was included in the transfection mix. Furthermore, the inhibitory effects of ΔC439-490 were specific. Inclusion of as much as 3 μg of ΔC439-490 did not lead to any change in the expression of the internal reference plasmid pMSVtk.

The results outlined in the preceeding paragraph raised the possibility that some portion of the polypeptide encoded by ΔC439-490 caused a specific inhibition of VP16-mediated trans-induction. To investigate this phenomenon in more detail, additional deletion mutants of VP16 were constructed as a means of defining the inhibitory domain. The strategy was to begin with a fully inhibitory molecule (lacking the carboxyl-terminal 78 amino acids of VP16), pare it down by in vitro mutagenesis, then test the ability of mutated variants to inhibit the activity of the native inducer. Deletion of the starting template (ΔC413-490) was initiated from two locations. In one case, additional carboxyl-terminal codons were removed (termed ΔC' mutants). Although 12 such mutants were constructed to evenly cover 30 kilodaltons of the protein, only the least truncated mutants proved to be useful. ΔC'392 inhibited the trans-activating potential of native VP16 to an intermediate degree, whereas ΔC'380, ΔC'363 and all other mutants failed to interfere. Western blot analysis of the products of the mutagenized templates revealed that only the starting plasmid (ΔC412-490) and its least truncated variant (ΔC'392) produced immunoreactive protein.

A second series of deletions was prepared from ΔC412-490 starting near the amino terminus of the VP16 ORF (see FIG. 1). In this series, termed ΔN'C, each mutant retained a fixed boundary four codons downstream from the first methionine codon of the ORF, and a variable boundary extending towards the carboxyl terminus of the protein. Twelve mutants were prepared to evenly span roughly 30 kilodaltons of the protein. Again, only the least deleted mutants provided useful information. ΔN'C5-41, which encoded a protein lacking 36 amino acids near the amino terminus (in addition to the 78 carboxyl terminal amino acids), interfered potently with VP16 action. ΔN'C5-56, which lacks 51 codons, showed an intermediate capacity to interfere. Finally, ΔN'C5-74, and all additional members of the ΔN'C deletion series, were unable to interfere with VP16-mediated trans-induction.

The deletion studies described in the preceding paragraphs indicated that an extended region of the protein must remain intact in order to support the interference phenomenon. Near the amino terminus, a boundary critical to interference occurred between codons 56 and 74. Near the carboxyl terminus, a boundary was observed between codons 380 and 393. When re-attached to the acidic tail, ΔN'C5-41 activated potently, ΔN'C5-56 and aC'393 activated to an intermediate degree, and all other mutants failed to activate IE gene transcription. These results, which are summarized schematically in FIG. 6, support the legitimacy of the dominant interference assay.

The results demonstrate the existence of two functionally distinguishable domains within the VP16 polypeptide. A domain localized within the carboxyl terminal 78 codons of the VP16 ORF, which is unusually rich in acidic amino acids, is critical to the transcriptional activating function of VP16. A second domain integral to the function of VP16 occurs N-terminal to its acidic tail. In the absence of the acidic tail, this N-terminal segment acts to dominantly and specifically interfere with the native inducer. That is, expression of the "tail-deleted" form of VP16 fully abrogates the capacity of the intact inducer to trans-activate IE gene expression, but does not interfere with the function of enhancers that are not VP16-responsive. It is expected that the truncated VP16 molecule retains the ability to interact with the cellular factors that bond IE cis-regulatory DNA sequences and in so doing competitively inhibit interaction with native VP16.

EXAMPLE 2

Expression of Dominant Form of Viral Trans-Activator in Mammalian Cells and Selective Impairment of Lyric Infection by the Cognate Virus As indicated in Example 1, removal of the carboxyl terminal 78 amino acids of VP16 not only eliminates activation function of the protein, but also results in a form of the protein that dominantly interferes with the native activator. The truncated protein apparently retains the capacity to interact specifically with the cellular DNA binding proteins that mediate interaction with IE cis-regulatory sequences and in so doing saturate interaction sites on cellular DNA binding proteins, thereby blocking occupancy of these sites by native VP16 protein. An important aspect of the trans-dominance of the tail-truncated form of VP16 is its specificity. Expression of tail-truncated VP16 does not interfere with the utilization of cis-regulatory elements that are not targets of VP16 action.

To demonstrate that constitutive expression of the tail-truncated form of the activator would, by blocking the function of the natural activator, impair the HSV lytic cycle, stably transformed cell lines that express tail-truncated VP16 were prepared. LMtk mouse L cells were co-transfected with two bacterial plasmids. One plasmid contained a recombinant copy of the HSV thymidine kinase (tk) gene, and the other contained a recombinant copy of the HSV gene that encodes VP16. In the latter case, the promoter of the VP16 gene was replaced by that of the Moloney Murine Sarcoma Virus (MSV) long terminal repeat (LTR), and DNA sequences encoding the carboxyl terminal 78 amino acids of the VP16 polypeptide were deleted. Stable, tk-positive, transformant colonies were identified by selection in HAT medium, and 42 clones were tested by indirect immunofluorescence for VP16 expression. Roughly half of the clones proved positive in this assay, and in all cases the antigenic signal detected by immunofluorescence was localized in nuclei. The immunofluorescent staining pattern of a VP16-positive transformant (line 4) was compared with that of a line transformed with the HSV tk gene alone (line 1). Western blot analyses were consistent with the cytological pattern of antibody reactivity, and provided evidence that antigen-positive line 4 produced the appropriately truncated form of VP16.

Three tests were performed to examine the growth of HSV on cells that expressed tail-truncated VP16. First, the viral infectious cycle was followed by light microscopy in order to track pathogenic effects. Cells that expressed tail-truncated VP16 (line 4) showed minimal evidence of viral pathogenesis under conditions of infection that were uniformly lethal to control cells (line 1). Second, the experimental and control cell lines were compared for their capacity to support formation of viral plaques. In this assay, line 1 supported plaque formation, while line 4 did not. Third, virus production in control and experimental cells was monitored over a time course of infection. Cells were infected with either HSV or pseudorabies virus (PRV) and culture medium was retrieved at successive intervals post-infection for virus titer assays. PRV was chosen as a control virus since it is very closely related to HSV, yet does not encode any IE activating factor related to VP16. The results demonstrated that line 4 was selectively defective, relative to line 1, in its capacity to support lytic growth of HSV (PRV grew equally well on the two cell lines). That is, the growth curves demonstrated a lag in the initial appearance of newly made virus (8–10 hr), and a reduction in the amount of virus produced over a time period sufficient for a single lytic infectious cycle (roughly 25-fold reduction in virus titer 24 hr post infection).

The fact that the lytic growth of PRV in line 4 could not be distinguished from the control cell line indicates that the observed effects of tail-truncated VP16 on HSV growth were not simply a result of deleterious effects on the growth properties or viability of line 4. This possibility was also tested by comparing the doubling times of the experimental cell line with the control cell line that did not express the truncated activator. The two lines grow at an indistinguishable rate, one cell doubling every 19 hours.

The foregoing invention has been described in some detail by way of Examples for purposes of clarity and understanding. It will be obvious that various combinations in form and detail can be made without departing from the scope of the invention.

What is claimed is:

1. A method of specifically inhibiting growth of a virus, that is a member of the family Herpesviridae, in a permissive mammalian host cell comprising:

i) introducing into said cell a gene encoding a carboxyl-terminal truncated form of VP16 lacking activation function; and ii) causing expression of said gene and thereby production of said form of VP16 so that growth of said virus is inhibited.

2. The method according to claim 1 wherein said virus is herpes simplex virus.

3. A method of specifically inhibiting growth of a virus that is a member of the family Herpes viridae in a permissive mammalian host cell comprising:

i) introducing into said cell a virus-related gene encoding a protein capable of specifically interacting with a product encoded in the genome of said virus so that the life cycle of said virus is disrupted; and ii) causing expression of said virus-related gene and interaction of said protein with said product encoded in the genome of said virus;

said product encoded in the virus related gene is a trans-dominant form of a viral activator and said viral activator is a form of the HSV-specific activator VP16 lacking the activating domain.

* * * * *